United States Patent [19]

Nam

[11] Patent Number: 5,716,649
[45] Date of Patent: Feb. 10, 1998

[54] PROCESS OF INCREASING CALCIUM CONTENT IN AN AQUEOUS SOLUTION

[76] Inventor: Wal Hee Nam, 1015 N. Kingsley Dr. #325, Los Angeles, Calif. 90029

[21] Appl. No.: 821,286

[22] Filed: Mar. 20, 1997

[51] Int. Cl.$^6$ .......................... A61K 33/10; A61K 33/00; A61K 33/06; A61K 33/24

[52] U.S. Cl. .......................... 424/687; 424/650; 424/682; 424/686; 424/688; 424/693; 424/715; 424/724

[58] Field of Search .................... 424/687, 650, 424/682, 686, 688, 693, 715, 724, 722; 426/66, 74; 514/905

[56] References Cited

U.S. PATENT DOCUMENTS

| | | | |
|---|---|---|---|
| 4,325,975 | 4/1982 | Lindon et al. | 426/66 |
| 5,045,323 | 9/1991 | Michalek | 424/601 |
| 5,620,709 | 4/1997 | Kumagai et al. | 424/682 |

FOREIGN PATENT DOCUMENTS 58-74610  5/1983  Japan.

OTHER PUBLICATIONS

Martindale The Extra Pharmacopoeia, 13th ed., The Pharmaceutical Press, London, pp. 853–856, 1993.

*Primary Examiner*—John Pak
*Attorney, Agent, or Firm*—Eugene Oak

[57] ABSTRACT

A batch process for increasing the calcium content of a water solution comprises the placement of a tin catalyst, a glass fibrous material, and water into a sealed tank and the application of heat to the tank for predetermined time intervals at progressively decreasing temperatures. The resulting solution is then extracted from the tank, wherein the solution has between 200 ppm and 500 ppm concentration of calcium.

3 Claims, No Drawings

PROCESS OF INCREASING CALCIUM CONTENT IN AN AQUEOUS SOLUTION

BACKGROUND OF THE INVENTION

1. Field of the Invention

The present invention relates generally to the dissolution of salts in aqueous solutions, and in particular to a batch process for increasing the amount of dissolved calcium in water.

2. Description of the Prior Art

The prior art teaches different processes of introducing salts and other matter into aqueous solutions. However, none of these processes disclose a process as taught by the present invention.

Accordingly, the principle object of the present invention is to provide a process which increases the amount of calcium found in conventional water.

Another object of the present invention is to provide a process which yields a calcium aqueous solution which may be beneficial to one's health when ingested.

Yet another object of the present invention is to provide a process which is relatively inexpensive to maintain.

SUMMARY OF THE INVENTION

It is commonly understood that calcium is necessary to maintain a healthy body. Until now, main sources of calcium include milk and other dairy products and vitamin supplements. While many people suffer from lactose intolerance and others refrain from the oral ingestion of large and unsightly pills and vitamins, the present invention provides water which has a high calcium content which has beneficial effects on the human body.

The present invention discloses a batch process in which high amounts of calcium may be dissolved into water thereby resulting in an aqueous solution which is intended for oral ingestion. The equipment necessary for the process is a stainless steel mixing tank, a tin catalyst, and a glass fiber which further comprises 75% silica, 20% soda ash, and 5% limestone. Approximately 50 gallons of water free of contaminants is fed into the stainless steel mixing tank. The tin catalyst and glass fiber are also placed inside the tank and the tank is sealed and the water is heated at 80° C. for 15 days. The temperature is slowly decreased to room temperature within the next 135 days, and the solution is removed. The resulting solution has a relatively high concentration of calcium at about 390 ppm.

These together with other objects of the invention are explained clearly in the claims annexed to and forming a part of this disclosure. For a better understanding of the present invention, its operating advantages and the specific objects attained by its use, reference should be made to the following descriptive matter in which there is illustrated preferred embodiments of the present invention.

DETAILED DESCRIPTION OF THE PREFERRED EMBODIMENT

The present invention increases the calcium content in a water solution. Water is added to a stainless steel tank. Inside the tank is a solid catalyst comprising 75 wt % tin, 15 wt % soda ash, and 10 wt % limestone. The catalyst is of a disc-like shape and may be porous to increase the surface area of reaction. In addition, a glass fibrous material comprising 75 wt % silica, 20 wt % soda ash, and 5 wt % limestone is placed into the tank.

The tank is sealed from the atmosphere and the temperature within the tank is controlled at 80° C. for fifteen (15) days. The temperature within the tank is then reduced to 60° C. and maintained for another fifteen (15) days. The temperature within the tank is then reduced to 40° C. and maintained for thirty (30) days. The temperature within the tank is then reduced to 30° C. and maintained for thirty (30) more days. Finally, the temperature within the tank is reduced to 0° C. and maintained for sixty (60) days. The tank is then opened and the resulting aqueous solution has a relatively high content of calcium. The aforementioned specified temperatures and the duration of application of heat are results of experimental experience. However, alterations of temperatures and the duration of application of heat may increase the resulting calcium content of the solution.

Tests were taken of solutions which were prepared in the aforementioned manner at Milliker Laboratories of Calif. on Nov. 8, 1993. The results showed that the solution had 390 ppm calcium content, a significant increase of calcium from conventional water. Altering the temperatures and the duration of the application of heat between 120 and 150 days results in solutions having calcium content between 200 ppm and 500 ppm.

The glass fibrous material and tin catalyst should be replaced every 50–70 batches, as the additional calcium content derives primarily from these two sources. An optimal ratio of water to glass fibrous material and tin catalyst is 1000 gallons of water to 50 kilograms of glass fibrous material and 150 kilograms of tin catalyst.

What is claimed as being new and therefore desired to be protected by letters patent of the United States is as follows:

1. A batch process for increasing the calcium content in a water solution, comprising placing water, a glass fibrous material and a tin catalyst in a sealed tank, and heating the tank to 80 degrees C. for 15 days and slowly decreasing the temperature of the tank for the next 135 days, wherein said glass fibrous material comprises 75 weight percent silica, 20 weight percent soda ash, and 5 weight percent limestone, wherein said tin catalyst comprises 75 weight percent tin, 10 weight percent limestone, and 15 weight percent soda ash.

2. A batch process for increasing the calcium content in a water solution as set forth in claim 1, wherein said sealed tank is maintained at 80 degrees C. for fifteen days, 60 degrees C. for another fifteen days, 40 degrees C. for thirty days, 30 degrees for another thirty days, and 0 degrees C. for sixty days.

3. A batch process for increasing the calcium content in a water solution as set forth in claim 1, wherein the ratio between water and said glass fibrous material is 1000 gallons to 50 kilograms, respectively, and wherein the ratio between water and said tin catalyst is 1000 gallons to 150 pounds, respectively.

* * * * *